United States Patent [19]

Sultanian et al.

[11] 4,107,284

[45] Aug. 15, 1978

[54] RADIOIMMUNOASSAY PROCEDURE USING A STABILIZED COMPLEX

[76] Inventors: Ishkhan V. Sultanian, 2729 Sandpiper Ave., Costa Mesa, Calif. 92626; Joseph H. Irani, 3207 Broad St., Newport Beach, Calif. 92663

[21] Appl. No.: 626,228

[22] Filed: Oct. 28, 1975

[51] Int. Cl.$^2$ .................. A61K 43/00; G01N 33/00
[52] U.S. Cl. ........................... 424/1; 23/230 B
[58] Field of Search ............... 23/230 B, 230.6; 424/1, 424/1.5, 12

[56] References Cited

U.S. PATENT DOCUMENTS

| | | | |
|---|---|---|---|
| 3,911,096 | 10/1975 | Chopra | 424/1 |
| 3,928,553 | 12/1975 | Hollander | 424/1 |

*Primary Examiner*—Benjamin R. Padgett
*Assistant Examiner*—Christine M. Nucker
*Attorney, Agent, or Firm*—Mario A. Martella

[57] ABSTRACT

An improved radioimmunoassay procedure involves the use of a stabilized complex of labelled antigen and antibody which has an extended shelf life as compared to the same complex absent the stabilizers. Since the time needed to incubate the mixture of labelled antigen and antibody is eliminated, the time for completing the assay is considerably shortened and simplified. The components for carrying out the procedure are packaged in a kit basically including standard antigen for generation of a standard curve, a stabilized labelled antigen-antibody complex and reference serum, if used. A plurality of stabilizers are used in the complex to provide a shelf life of six weeks or more.

10 Claims, No Drawings

RADIOIMMUNOASSAY PROCEDURE USING A STABILIZED COMPLEX

STATE OF THE ART

Radioimmunoassay is a known analytical technique structured around the immunological phenomenon of antigen binding or affinity to specific antibodies. While usually regarded as fairly specific, i.e. the antigen will only bind or compete for the binding sites available on the antibody, antigens may bind to some protein other than the antibody. In an analytical procedure in which nano- and pico-gram quantities are determined, this may create errors in the assay usually conducted by comparison with a standard curve.

More specifically, unknown concentrations of antigens may be accurately determined in nano- and picogram quantities from the observation that labelled antigen competes with the unknown non-labelled antigen for the binding sites on the antibody. Normally a standard antigen is also used, i.e. an unlabelled antigen of known concentration used to generate the standard curve. The procedure normally requires that the unknown antigen and the standard behave identically in their ability to displace labelled antigen from a labelled antigen and antibody complex, but not identical behaviour between the labelled, the unknown and the standard. Normally, the labelled antigen and antibody are premixed, allowed to incubate to permit the antigen to bind to the antibody.

For example, if increasing amounts of unlabelled antigen are added to the antibody, the antibody binding sites are saturated and binds less labelled antigen. Thus, the procedure usually involves binding the tracer to the antibody in the absence of the standard and unknown antigen. When the standard or unknown are brought into contact with the labelled antigen-antibody complex, an equilibration takes place in which the labelled antigen and the unknown and standard antigen compete for the binding sites on the antibody. The free unbound antigen is then separated and counted for radioactivity. By comparison with standard curves, generated from the standards, the concentration of the unknown is determined.

Kits are known for use in assay procedures which include separately packaged components such as an antibody, a radioactive tracer labelled antigen, standard unlabelled antigen and material to effect separation of the unbound antigen. With such kits, the labelled antigen is mixed with the antibody prior to use of the kit, so as to form the complex which is then used in the assay. Formation of the complex takes some period of time, and if not used tends to become unstable. The incubation period may vary from 15 minutes to 2 hours or more. Once formed, the complex usually is used promptly since the shelf life of the formed complex is somewhat limited. The difficulty which is encountered is that the specificity of the antibody is changed, i.e. tends to become nonspecific and the antigen tends to bind to a protein other than the antibody in the complex. Where an antigen of unknown quantity is in the presence of other proteins, for example, in serum, degeneration of the specific binding activity of the antibody portion of the complex may lead to erronious test data. Specifically, as the tendency for nonspecific binding increases, the test results become correspondingly poorer.

It is known to use a single inhibitor to inhibit or which masks the sites on proteins other than the sites on the antibody. Such a procedure, however, provides some stability for only a short time, the result is that the complex must be formed immediately prior to use, in order to assure the desired specific activity, with resultant increase in time to perform the assay. As already noted, incubation time may be as long as two hours or more to form the complex. While relatively large amounts of complex may be formed, this can only be done if the need to use the specific complex can be accurately forecast. If the forecast is inaccurate, there is waste of complex or use of "stale" complex leading to erronious testing. The tendancy, for good reason, is to be conservative and to discard any complex which is likely to be stale.

Accordingly, the provision of a complex of relatively long life is desirable since it reduces the time necessary for incubation at the using facility. One result is a significant reduction in the actual time to run the assay procedure.

Another advantage of the provision of a relatively stable complex, e.g. one having a useful "shelf life" of six weeks in that the burden of accurate forecasts of need by the using facility is somewhat reduced. With such a shelf life, any facility performing the assay may store a kit with a premixed, preincubated relatively stable complex and known reliably the expected life, especially if the date of expiration can be determined with certainty.

DESCRIPTION OF THE PRIOR ART

U.S. Pat. No. 3,555,143 of Jan. 12, 1971, describes a radioimmunoassay procedure in which long incubation periods are used, e.g. 20 hours or more.

Kits are also known in which the radioactive labelled antigen is packaged separately from the antibody and then mixed prior to use and incubated for a period of time sufficient to reach equilibrium. The period of incubation may vary from 2 to 3 hours. For example, such a kit used in the assay of thyroxine requires about 2 to 3 hours for the procedure due to the incubation time for complex formation.

It is also known that 8-aniline-1-naphthalenesulfonic acid may be used to mobilize thyroxine from its binding with thyroxine binding globulin. A barbital buffer has also been used to inhibit the binding of thyroxine to thyroxine binding prealbumin. See Chopra, I.J. (1972) *J. Clin Endrocrinal, Metab.* 34:938. Such use, however, does not provide a long shelf life which allows prepackaging of the formed complex.

SUMMARY OF THE INVENTION

This invention relates to radioimmunoassay and more particularly to an improved assay procedure using a preincubated, relatively stable complex and to the complex itself.

By the present invention, a kit is provided for radioimmunoassay which includes a stabilized antibody—labelled antigen complex, standard antigen and separating media. The procedure involves simultaneous assays of the unknown and standard antigen, generation of a standard curve and use of the standard curve to determine the amount of the unknown antigen. The unknown antigen may be in the form of serum samples or extracted antigen. The unknown and each of the standards are added to separate tubes and the antigen-antibody complex is added to each tube. Since the complex is stable and preformed, no premixing and incubation is necessary. The mixture of complex and unknown antigen and standard antigen are then incubated and the unbound antigen is separated and counted. From the counts of the standards a standard curve is generated for use in determination of the concentration of the unknown antigen. By this procedure, microgram, nanogram, and picogram quantities of various antigen may be determined by a procedure which takes less time than other comparable procedures because the incubation time needed to form the complex is eliminated.

The complex itself includes a plurality of stabilizers which operate to impart a stability to the complex which it normally would not have if only the labelled antigen and antibody were mixed and incubated. The stabilizers include effective amounts of 8-anilino-1-naphthalenesulfonic acid in the form of a sodium salt, merthiolate, ferrous sulfate and M,N-dimethyl-p-phenylenediamine dihydro chloride. These stabilizers are present in an amount up to 2% and operate to inhibit the tendency of the antigen to associate with protein other than the antibody.

In the formation of the complex, before packaging the same, the components making up the stabilized complex are admixed and incubated overnight in a refrigerator in order to achieve an equilibrium condition.

DETAILED DESCRIPTION OF THE INVENTION

In accordance with a preferred form of this invention, a kit is provided the important component of which is a preincubated stabilized radioactive isotope labelled antigen-antibody complex. As is known, radioimmunoassay procedures are based on the specific immunological reactions of antigen and antibody. Normally, the antigen is labelled and competes with the antigen in the sample for the binding sites on the antibody. Thus, the assay depends on the antigen exchanging with the labelled antigen. If the antigen binds to a protein other than the antibody, that is, fails to exchange with the labelled antigen, the assay results are in error.

As stated the usual procedure is to premix the labelled antigen and antibody prior to use but this is time consuming because of the incubation period needed to reach an equilibrium condition. Once mixed, the complex has limited shelf life and the tendency of the antigen to bind to a protein other than the antibody increases thus adversely affecting the exchange needed for accurate assays in the micro-, nano-, and pico-gram range.

By this invention a complex is provided which is stabilized thus enabling the kit to include a prepackaged stable complex with a reasonable shelf life. The time of the actual assay procedure is reduced by eliminating the incubation step normally needed to form the complex.

Thus, several stabilizers are compounded with the labelled antigen-antibody complex to prolong the usable shelf life thereof to from four to six weeks after compounding. This relatively long shelf life is achievably the use of effective amounts of a plurality of stabilizers such as 8-anilino-1-naphthalenesulfonic acid in the form of the sodium salt, merthiolate, ferrous sulfate and N-N-dimethyl-p-phenylene diamine dihydro chloride, all of which are water soluble.

In one form, the complex of this invention is packaged in quantities of 10 to 25 milliliters with each such tube including 50 microliters of each of a 1% 8-anilino-1-naphthalene sulfonic acid in water, 0.1% solution of merthiolate, 2% solution of ferrous sulfate and 2% solution of N,N-dimethyl-p-phenylenediamine dihydro chloride, all percentages being by weight. In these relative amounts, the described stabilizers are operative to provide a shelf life of four to six weeks. The preparation of the stabilized complex involved adding the stabilizers in the relative amounts indicated and incubating the mixture overnight at 4° C.

The remaining components of the kit include standards of known quantities of antigen used to generate standard curves. These standards are free of serum and in some instances it is desirable to provide reference serum, i.e. human serum containing known amounts of antigen used as a check of the standards due to the possibility that the complex may behave differently to the standards and the reference sera, in which event the data generated by the reference sera is used as the standard.

Also optionally included in the kit is a reagent to effect separation of the bound and unbound antigen. One such reagent is charcoal coated with dextran, normally separately packaged and mixed prior to use.

The usual procedure in accordance with this invention is to run each sample, including unknown, standards, and reference sera in duplicate. Accurate pipetting is important since the assay is run on an alignment basis.

In general the procedure of this invention involves using a known volume of patient sera with known volumes of reagents, relatively short incubation of the antigen (standard, unknown, and optionally the reference sera) with the stabilized complex, addition of the separating agent, centrifuging, removal of the supernatant and counting the unbound antigen which remains with the separating agent. The counts from the standard (or optionally reference sera) are used to plot a curve against which the counts of the unknown are compared to provide concentration of the unknown.

It is possible to count the bound antigen but this is a more difficult procedure and thus it is preferred to count the unbound.

Charcoal coated with dextran is used since it operates to absorb the unbound antigen, i.e. the antigen which is not bound to the antibody. Dextran of molecular weight between 10,000 to 250,000 may be used depending on the molecular weight of the unbound antigen. The dextran, a glucose polymer, forms a matrix which permits passage of the smaller molecular weight materials such as the unbound antigen, the bound antigen being of substantially greater molecular weight due to the antibody. Once through the matrix, the unbound antigen is adsorbed on the charcoal. It is easier to take a radio active count of the charcoal component rather than the supernatant and for this reason it is the preferred form in this invention.

When the antigen is mixed with the stabilized labelled antigen-antibody complex, the mixture is incubated to permit equilibration, i.e. exchange of unknown with labelled antigen. The amount of labelled antigen which is freed from the antibody is directly related to the amount of antigen in the unknown. The greater the amount in the unknown, the greater the amount of labelled antigen which is freed, for a complex of given antibody activity. Thus, the standards and reference sera are used to form a standard curve since the complex is of the same activity as that used with the unknown due to the alignment procedure.

The advantages of this invention stem from the provision of a stabilized complex which eliminates the step of incubation needed to form a labelled antigen-antibody complex. Moreover, if not completely used in a given assay, the stabilized complex of the present invention may be stored at 4° C. for later use and need not be discarded because of the relatively long useful life provided by the stabilizer.

The radioactive isotopes used in this invention may be $I^{125}$ of $H^3$ depending on the nature of the antigen. Many labelled antigens are known and available, for example, triiodothyronine $I^{125}$, thyroxine $I^{125}$, cortisol $H^3$, estradiol $H^3$, gentamicin $H^3$, and estrone $H^3$, only to mention a few. The present invention has application not only to the assay of the above antigen but to others as well.

The counter used for radioactive counting may be a gamma counter having an accuracy of I 5% for use with $I^{125}$ isotopes or a beta counter for use with $H^3$.

The following are examples of typical embodiments of the invention and illustrative thereof.

EXAMPLE 1

The levels of circulating triiodothyronine, sometimes referred to as T-3, in blood contributes to metabolic effects of thyrohormones. It is a useful adjunct in diagnosing diseases such as Graves, T-3 thyrotoxicity and in assessing thyroid reserve.

The kit, in accordance with this invention includes:

(1) Two vials (10.0 ml each) of T-3 antibody-antigen complex with labelled ($I^{125}$) antigen;

(2) Five vials (2.0 ml each) of T-3 standard (0, 75, 150, 300, 400 picogram/ml);

(3) One bottle (15 ml) of charcoal dispersion, 1.8% charcoal by volume; and (4) One bottle (15 ml) dextran solution, 0.18% dextran by volume. The antibody-antigen complex is stabilized with the stabilizers already identified and present in the amounts indicated. With reagents stored at 4° C., the shelf life is four to six weeks after packaging.

As noted earlier, accurate pipetting is important in the procedure. In a preferred form, each of the samples is run in duplicate.

By way of preparation, serum samples are diluted in the ratio of one to ten with physiological saline solution having a pH of 7.4. This step may be eliminated if 20 microliters of serum sample plus 180 microliters of saline is directly added to the appropriately labelled test tubes. The standard solutions provided in the kit are already prepared and need not be diluted further. If the kit is to be used over a period exceeding one week, aliquots of 200 microliter amounts of the standards may be introduced into appropriately labelled tubes and stored frozen until needed. The charcoal dextran slurry is prepared by mixing equal amounts of the charcoal and dextran solutions, approximately 200 microliters of the slurry being needed for each assay tube. The slurry can be prepared during the incubation period to be described. The slurry should be stored at 4° C and should be made up fresh. Prior to the actual assay, all of the reagents except the slurry should be brought to room temperature (15°–30° C) and shaken well before use.

Approximately 200 microliters of the saline diluted serum is added to each of the glass tubes. To each of five prepared standard tubes is added 200 microliters of each of the five standards. 200 microliters of the stabilized complex is added to each of the tubes and shaken for 10 to 20 times and incubated in the tubes at 37° C for about two hours. Thereafter, 200 microliters of the charcoal-dextran slurry is added to each tube, care being taken to shake the slurry well while dispensing. The tubes are then shaken 10 to 20 times and incubated at 4° C for 30 minutes.

Each of the tubes is centrifuged in the same centrifuge at 2,000 rpm for 15 minutes. The supernatant is aspirated from each tube and a radioactive count of the deposit is taken for the activity. A gamma counter should be used and counting should be conducted for at least one minute.

It is preferred that the counting step be conducted a few minutes after the aspiration step, however, the tubes can be capped and stored at 4° C for later counting. The tubes may be stored for one month, and counted at a later time within the one month period as desired.

The counting of the charcoal deposits represents a count of the unbound T-3. By plotting the counts directly on linear graph paper, using as the origin of the graph the standard O counts, the increasing counts are plotted along the vertical axis. Using the usual procedure, the background counts are subtracted from the sample and standard counts. In this way, a plot is obtained of a standard curve representing the counts of the unbound antigen as the vertical axis and the standard nanagrams per mililiter of antigen as the horizontal axis, the points being connected by a curve. Thereafter, the samples of unknown are counted and read directly off the curve as nanagrams per hundred mililiters of T-3. For example, if the sample off the curve is 125 picograms per mililiter, then the T-3 concentration is 125 nanagrams per mililiter. The normal range of T-3 in serum is between 70 and 180 nanagrams per 100 mililiters.

EXAMPLE 2

The total thyroxine in blood is useful in assessing the levels of thyroid function. Increased levels of thyroxine have been found in hypothyrodism due to Graves' and Plummer's diseases, in accute and subaccute thyroiditis. Low levels of thyroxine, frequently referred to as T-4, have been associated with cretinism, myxedema, chronic thyroiditis (Hashimotos disease) and with genetic abnormalities.

The kit, in accordance with the present invention includes:

(1) One bottle (25 ml) of T-4 antibody-antigen complex with labelled ($I^{125}$) antigen:

(2) Five vials (250 ml each) of T-4 standard (0, 5, 10, 15, 25 nanograms/ml);

(3) Three vials (250 ml each) of reference serum—known amounts of T-4 in human serum;

(4) One bottle (25 ml) of charcoal-dextran slurry of a composition as already described in connection with Example 1.

In preparation for the assay, the charcoal-dextran slurry is premixed and stored at 4° C, and all reagants except the slurry are brought to room temperature (15°–30° C) and shaken before using.

Ten microliters of patient sera and 10 microliters of each of the five standard solutions and 10 microliters of the reference sera are added to each tube, each test being done in duplicate. To each tube 250 microliters of the complex is added and shaken for 10 to 20 times and then incubated in a water bath at 37° C for 30 minutes. Thereafter, 250 microliters of the slurry is added to each tube and shaken 10 to 20 times, care being taken to keep the slurry dispersed while dispensing into the tubes. Each tube is centifuged in the same centrifuge, preferably a swinging bucket type at 3,000 rpm for 15 minutes, or at 5,000 rpm for 5 minutes. The supernatant is aspirated or carefully decanted and a count is taken of the remaining pellet in a gamma counter for between 30 to 60 seconds.

Again, the counts should be taken shortly after aspiration or the tubes may be capped and stored at 4° C for later counting, but should not be stored for more than one month.

The counts of the charcoal deposits are counts of unbound T-4 and may be plotted directly on linear graph paper. The origin of the graph is the standard O counts with counts increasing along the vertical axis. Again, background counts should be subtracted from the standard and sample counts. The resulting plot provides a standard curve of counts of the unbound along the vertical axis versus standard micrograms per hundred mililiters along the horizontal axis. Thereafter, the counts of the unknown are read off the standard curve as micrograms per 100 mililiters of T-4. The normal range for T-4 is between 4.5 and 12.5 micrograms per hundred mililiters. Again, as noted in Example 1, the antibody-antigen complex was stabilized with the stabilizers already identified and present in the amounts indicated. The shelf life of the reagents, stored at 4° C is between 4 to 6 weeks after packaging.

Antigens such as cortisol, estradiol, gentamicin, and estrone may be quantitatively determined using radioimmunoassay in which the isotope is the tritium isotope. In each instance, the kit includes the stabilized complex, including the appropriate labelled antigen and specific antibody and the stabilizers in the amounts previously indicated. The procedures for each of these antigens is basically the same as the procedures described in Examples 1 and 2.

Cortisol is important in regulating the production of sugar from proteins. Its determination in plasma is a useful tool for the diagnosis and evaluation of Cushings Syndrome and adrenal insufficiency. Estrone and estriol are important in the evaluation of ovarian function and in other gynecological problems. Gentamicin monitoring is important in regulating the proper dosage of this antibiotic.

In the procedures previously identified, reference was made to a separating reagent in the form of dextran coated charcoal. In place thereof, one may use an anionic polystyrene resin such as polystyrene aminated with trimethylamine anion exchange resin, the particle size being between 20 and 50 mesh. Again, the amount retained on the solids represents the unbound antigen, and in this case, the activity may be counted on the resin, or on the eluate from the resin, and standard curves constructed as described.

As is apparent from the foregoing, one of the advantages of the present invention is the provision of a kit which has shelf life which is predictable and between four to six weeks from the date of packaging. Thus, the user can with certainty know or determine whether the complex is still sufficiently active to provide accurate data in the radioimmunoassay procedure. The other singular advantage which accrues is the reduction in the time involved in the actual assay itself since the incubation time needed to reach equilibrium in the formation of the complex is eliminated.

Thus, the provision of approximately 2% by weight of a multiple component stabilizer system provides a labelled antigen-antibody complex which vastly simplifies the procedure and offers considerable versatility in actual clinical use. Specifically, because of the shelf life of the prepackaged system, the user need not have to forecast accurately the future requirements for any specific kit since the shelf life is sufficiently long so that kits may be stored under appropriate conditions and used within the shelf life of the kit.

In the kits described, sufficient materials are provided for a hundred tube assays, and even if the kit is not entirely used in any particular assay, the components thereof may be stored at 4° C for from 4 to 6 weeks from the date of packaging. Such a stabilized complex offers considerable versatility and simplification of the procedure, definite practical advantages in radioimmunoassay procedures utilizing kit type systems.

While the present invention has been described in connection with the foregoing illustrative embodiments, it is to be understood that modifications, changes and alterations may be made without departing from the scope of the invention as defined in the apended claims.

We claim:

1. A stabilized radioactive isotope labelled antigen-antibody complex for use in radioimmunoassay procedures comprising:
   a mixture of a labelled antigen and an antibody specific to said antigen,
   said antigen being selected from the group consisting of triiodothyronine, thyroxine, thyroxine binding globulin, cortisol, estradiol, gentamicin and estrone, and
   a plurality of stabilizers present in said mixture in an amount effective to inhibit the labelled antigen from associating with protein other than said specific antibody.

2. A stabilized complex as set forth in claim 1 wherein said stabilizers comprise the sodium salt of 8-anilino-1-naphthalene sulfonic acid, merthiolate, ferrous sulfate and N-N-dimethyl-p-phenylenediamine dihydrochloride.

3. A stabilized complex as set forth in claim 1 wherein said stabilizers are present in an amount of 200 microliters per between 10 milliliters and 25 milliliters of complex, and each said stabilizer having a concentration of between 0.1% to 2.0% by weight.

4. A stabilized complex as set forth in claim 1 wherein said radioactive isotope is selected from the group consisting of $I^{125}$ and $H^3$.

5. A stabilized complex as set forth in claim 1 wherein said labelled antigen is selected from the group consisting of: $I^{125}$ labelled triiodothyronine, $I^{125}$ labelled thyroxine, $H^3$ labelled cortisol, $H^3$ labelled estradiol, $H^3$ labelled gentamicin, and $H^3$ labelled estrone.

6. A radioimmunoassay procedure for quantitatively determining the concentration of an antigen comprising the steps of:
   providing a stabilized radioactive isotope labelled antigen-antibody complex including a plurality of stabilizers present in an amount sufficient to provide a shelf life for said complex of between four to six weeks;
   admixing the antigen to be determined with said complex whereby a portion of the antigen to be determined becomes bound to the antibody of said complex, separating the complex and the antigen bound thereto from the unbound antigen, said antigen being selected from the group consisting of triiodothyronine, thyroxine, thyroxine binding globulin, cortisol, estradiol, gentamicin and estrone, and measuring the radioactivity at least of one of the bound or unbound antigen whereby the value of said radioactivity is a function of the quantity of the antigen to be determined.

7. A procedure as set forth in claim 6 wherein the quantity of the antigen is determined by reference to a standard curve.

8. A procedure as set forth in claim 6 wherein the radioactivity of the unbound antigen is measured.

9. A procedure as set forth in claim 6 wherein said stabilizers comprise the sodium salt of 8-anilino-1-naphthalene sulfonic acid, merthiolate, ferrous sulfate and N-N-dimethyl-p-phenylenediamine dihydrochloride.

10. A procedure as set forth in claim 6 wherein the radioactive isotope is selected from the group consisting of $I^{125}$ and $H^3$.

* * * * *